United States Patent [19]

Ochs

[11] Patent Number: 5,365,939
[45] Date of Patent: Nov. 22, 1994

[54] METHOD FOR EVALUATING AND TREATING AN INDIVIDUAL WITH ELECTROENCEPHALOGRAPHIC DISENTRAINMENT FEEDBACK

[75] Inventor: Len Ochs, Concord, Calif.

[73] Assignee: Neurotrain, L.C., Galveston, Tex.

[21] Appl. No.: 137,909

[22] Filed: Oct. 15, 1993

[51] Int. Cl.⁵ ............................................. A61B 5/0482
[52] U.S. Cl. ..................................... 128/732; 128/731
[58] Field of Search ......................................... 128/731.2

[56] References Cited

U.S. PATENT DOCUMENTS

| | | | |
|---|---|---|---|
| 5,036,858 | 8/1991 | Carter et al. | 128/732 |
| 5,076,281 | 12/1991 | Gavish | 128/732 X |
| 5,241,967 | 9/1993 | Yasushi et al. | 128/732 |

*Primary Examiner*—Angela D. Sykes
*Attorney, Agent, or Firm*—Timmons & Kelly

[57] ABSTRACT

A method for treating an individual by use of electroencephalographic feedback includes selecting a reference site for determining a brain wave frequency of the individual, entraining the brain wave frequency of the individual in one direction until a first predetermined stop condition occurs, and then entraining the brain wave frequency of the individual in the opposite direction until a second predetermined stop condition occurs. A method for assessing the flexibility of an individual with respect to treatment by electroencephalographic entrainment feedback includes selecting sites for determining brain wave frequencies of the individual, choosing one of the sites which has not been previously used for entrainment, entraining the brain wave frequency of the individual at the chosen site in one direction until a first predetermined stop condition occurs, entraining the brain wave frequency of the individual at the chosen site in the opposite direction until a second predetermined stop condition occurs, and then repeating the steps beginning with choosing a site until all sites have been tested.

6 Claims, 9 Drawing Sheets

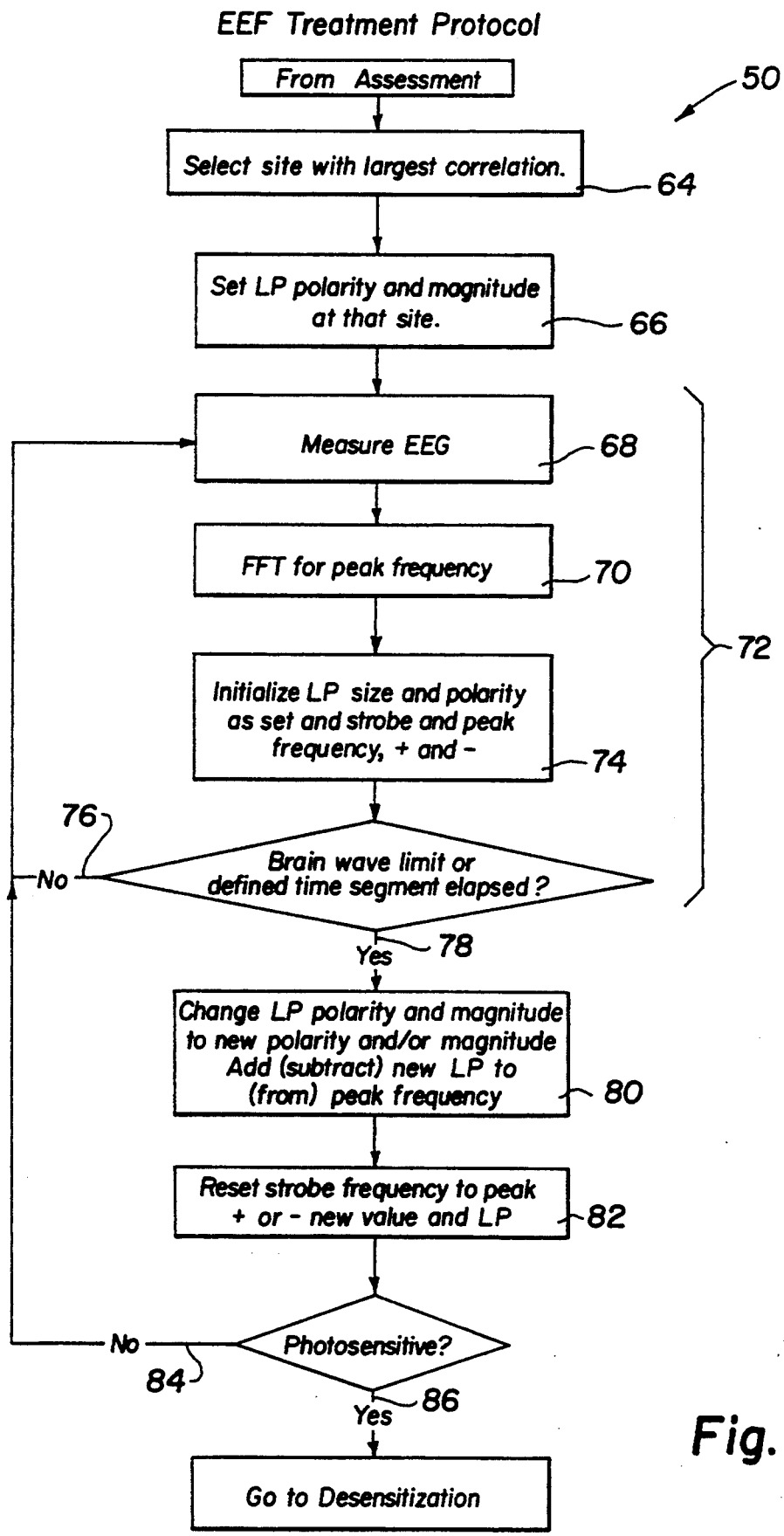

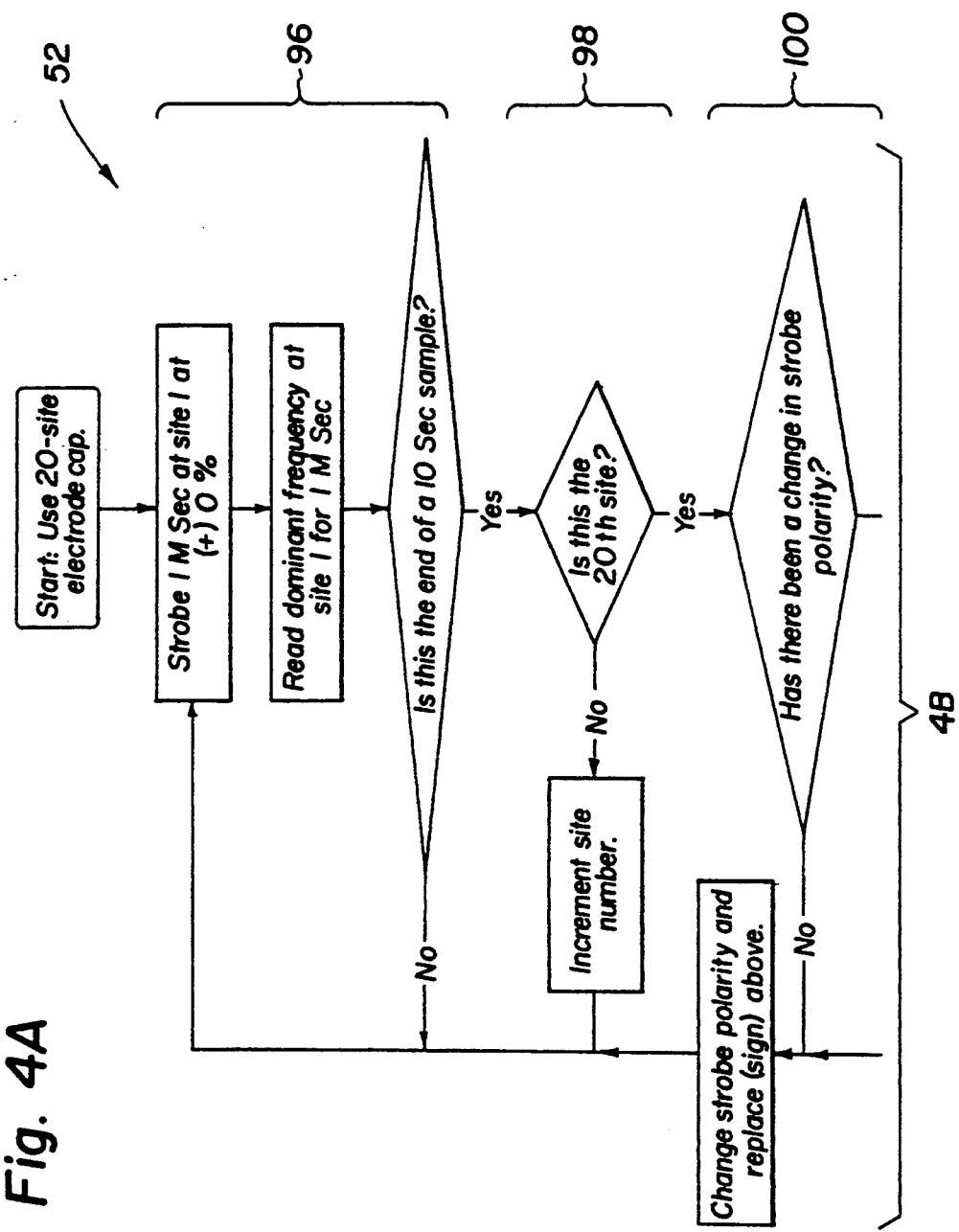

METHOD FOR EVALUATING AND TREATING AN INDIVIDUAL WITH ELECTROENCEPHALOGRAPHIC DISENTRAINMENT FEEDBACK

BACKGROUND OF THE INVENTION

1. Field of the Invention

The present invention relates generally to methods and apparatus for controlling brain wave frequencies and to therapeutic uses of such methods and apparatus.

Human brains disturbed by social, mechanical, chemical or other trauma become both restricted in their electrical and chemical activity and hypersensitive to internal and external events and stimuli. In one of its aspects, the present invention pertains to the assessment and amelioration of functioning after psychological and mechanical trauma, or the enhancement of typical brain functioning, through the disruption of the restriction and rigidity of neural activity.

2. Description of Related Art

In the 1960's and early 1970's, Robert Monroe of the Monroe Institute of Applied Sciences explored the effects of sound on the brain and discovered that he could produce a driving or entrainment of brain waves. Dr. Gerald Oster, a biophysicist, also investigating the effects of sound on the brain, discovered that pulsations called binaural beats occurred in the brain when tones of different frequencies were presented separately to each ear. The beat frequency equals the frequency difference between the two tones. Both Monroe and Oster began using electronic oscillators to provide tones with frequency, purity and intensity that can be precisely controlled.

U.S. Pat. No. 3,884,218 to Robert A. Monroe shows a method for inducing sleep by amplitude modulating a pleasing sound with a delta-rhythm signal which is referred to as an "EEG sleep signal."

U.S. Pat. No. 4,191,175 to Nagle shows a method and apparatus for repetitively "producing a noise-like signal for inducing a hypnotic or anesthetic effect. . ." by creating frequency bursts of digital pulses that are then passed through a pink noise filter to get rid of frequencies above a certain cut-off. The resultant signal is then passed through a band pass filter and used to drive an audible signal source.

An apparatus for electrophysiological stimulation is shown in U.S. Pat. No. 4,227,516 to Meland et al. in which a first signal above the delta-beta frequency range is modulated by signal within that range and applied to electrodes on the forehead of a user.

A learning-relaxation device of U.S. Pat. No. 4,315,502 has both lights for pulsing signals and sound means for a pulsing sound signal as well as a control means which can individually vary the light and sound signals.

U.S. Pat. No. 4,834,701 to Masaki shows a device similar to those used by Monroe and Oster with first and second generators with frequencies above 16 hertz and a frequency difference of 4 to 16 hertz sounded to lower the brain wave frequency of a user. The term "entrainment" began to be accepted for such devices: "This phenomenon, in which one regular cycle locks into another, is now called entrainment, or mode locking." (Gleick, *Chaos: Making of a New Science* 1987, Penguin Books, p. 293) An article entitled "Alpha Brain Waves & Biofeedback Training" in the December 1972 *Popular Electronics* show a system that uses a person's own EEG signal to modulate a tone generator which, in turn, then drives a speaker heard by the same person. The device allowed a person to "hear" his or her own brain signals in an attempt to voluntarily control the frequency. A similar device that allows a person to "see" his or her own brain waves is shown in an article entitled "Mind Power: Alpha" in the July 1976 *Radio-Electronics*.

U.S. Pat. No. 5,036,858 to John L. Carter and Harold L. Russell shows the use of EEG electrodes attached to the head of the user along with an amplifier for determining a current brain wave frequency of a user, which is communicated to a computer processor. A new frequency is generated which is between the current brain wave frequency and a desired brain wave frequency and is within a predetermined range of the current brain wave frequency. This has become known as electroencephalographic entrainment feedback if it is used to "lock" the current brain wave frequency into a desired frequency.

Prior methods for assessment of neural function involve radiographic, magnetic, electrical and nuclear evaluations with eyes open or eyes closed states, or at best, the neuronal or other activity evoked under different conditions such as reading, drawing, doing arithmetic, etc. Static frequency stimulation, even that steady frequency stimulation which alternates from time to time, is used to assess the presence and kind of seizure activity.

Methods of treatment have in many ways attempted to ameliorate brain functioning by either providing the brain with a faithful and accurate picture of its activity, or with a means of targeting a desired frequency, range of frequencies, or relationship among frequencies, or have targeted theoretically and empirically derived frequency states as a goal of training or therapy. Methods using feedback have largely involved conscious, voluntary processes in the amelioration of neural functioning. Such methods have not fitted the stimulation frequencies to real-time measurements of neural frequency. They have taken as a goal to feedback to the brain information as to success at reaching target neural activity. These methods require conscious attention, concentration, analysis and learning.

SUMMARY OF THE INVENTION

"Disentrainment" is a term coined by the present inventor to refer to the disruption of entrained brain wave patterns, patterns which have become in some way locked. As opposed to entrainment, disentrainment is more a process that leads to the re-establishment of biological systems flexibility. As critical as the ability of a system in its ability to withstand shocks is "how well a system can function over a range of frequencies. A locking-in to a single mode can be enslavement, preventing a system from adapting to change . . . . [N]o heartbeat or respiratory rhythm can be locked into the strict periodicities of the simplest physical models, and the same is true of the subtler rhythms of the rest of the body." (Gleick, 1987, p. 293, italics author's) The EDF system according to the present invention makes more flexible a range of neurological and neurochemical systems and consequently improves conditions of patients once thought to be largely hopeless.

A method for treating an individual according to the present invention is to use electroencephalographic disentrainment feedback to "exercise" the individual's brain. One such method includes first determining a reference site for determining a brain wave frequency of the individual and placing an EEG electrode to the head of the user at that site or where the brain wave of that site may be read. Frequently, simply placing the electrode near the center of the individual's forehead gives satisfactory results which are near the dominant brain wave frequency.

A first sequence of steps is then begun, including producing a stimulation detectible by the individual with a frequency component that is a transform of the brain wave frequency. The frequency component may be at a predetermined difference from the brain wave frequency. Such a transform may include, but not be limited to, a compression, expansion, phase difference, statistical sampling or time delay from the brain wave frequency. Such a stimulation can be of the conventional sort through light goggles or earphones. A strobe light can be produced through the goggles or externally as long as it is sufficiently bright to the individual. The difference could be either plus or minus, one is simply picked to be the first polarity, determining if the entrainment is to first lead the brain wave frequency to a higher or a lower frequency.

If a first predetermined time has not elapsed from the initiation of the first sequence of steps and the brain wave frequency has not reached a first limit corresponding to the first polarity, then the first sequence of steps is repeated. If, on the other hand, the first predetermined time has elapsed or the brain wave frequency has reached the first limit, then a second sequence of steps is begun. Either the first or the second sequence of steps can be stopped upon a predetermined stop condition such as end of the session or an adverse reaction by the individual. The process is then repeated in the other direction. If the first polarity was positive, entraining the individual's brain wave frequency higher, a reasonable upper limit would be around thirty hertz or even as high as forty hertz. Once that upper limit is reached or the process is timed out in the first direction, the polarity would be changed to negative and the individual's brain wave would then be entrained downwardly to a second limit, perhaps as low as two hertz.

Some individuals exhibit extreme sensitivity to flickering or strobe type lights. In some, such lights can even induce seizures. The person administering treatment needs to remain alert to any symptoms of hypersensitivity. Certain procedures are built into a preferred process when a strobe is used. The strobe frequency is set in the normal way using the leading percentage size and polarity as set. If the individual does not exhibit signs of being photosensitive, then the first sequence of steps is repeated as before. If, on the other hand, the individual does exhibit signs of being photosensitive, and the lower and mid frequency activity slopes with respect to time are positive, then the intensity of the stimulation is reduced until the slopes are zero or negative. If the individual continues to exhibit signs of being photosensitive, and the lower and mid frequency activity slopes with respect to time continue to be positive, then the frequency excursion limits are reduced until the slopes are zero or negative. If the individual continues to exhibit signs of being photosensitive, the alternating positive and negative polarities are replaced by either positive or negative polarity without alternation, depending on whether the person is hypersensitive to lower or higher frequencies respectively. If the individual still continues to exhibit signs of being photosensitive, then treatment is stopped.

A method according to the present invention for assessing the flexibility of an individual with respect to treatment by brain wave variation involves testing several sites on the head of the individual. The first step is to select an initial site for determining a brain wave frequency of the individual. Stimulation detectible by the individual is begun with a frequency component at an initial difference from the brain wave frequency, the difference being at a first polarity as before. A sequence of steps is started by recording the brain wave frequency at the selected site. If the predetermined sites have not all been selected for the current frequency and polarity, then use a site that has not been selected and repeat the sequence of steps from the beginning. If the predetermined sites have all been selected for the current frequency and polarity, then determine if there has been a polarity change for the current frequency. If there has not been a change in polarity for the current frequency, then change the polarity and repeat the sequence of steps from the beginning. If, to the contrary, there has been a change in polarity for the current frequency, then determine if there has been a change in the difference in frequency. If there has not been a change in the difference in frequency, then increase the difference in frequency by a first predetermined amount or a first predetermined percentage, change the polarity and repeat the sequence of steps from the beginning. If there has been a change in the difference in frequency, then determine if the difference in frequency is less than a second predetermined amount or a second predetermined percentage. If the difference in frequency is not less than the second predetermined amount or the second predetermined percentage, then increase the difference in frequency by the first predetermined amount or the first predetermined percentage, change the polarity and repeat the sequence of steps from the beginning. If the difference in frequency is less than the second predetermined amount or the second predetermined percentage, then make a determination of flexibility according to predetermined criteria. Such criteria might depend on how rapidly the brain of the individual entrains or how far the maximum excursion extends for different sites.

It is an object of the method of treatment according to the present invention to modify both suboptimal and gross post-traumatic neural functioning, which in the past were modifiable only with great difficulty because they are neurologically locked.

The assessment method according to the present invention evaluates neuronal flexibility and maps it in many graphical forms and mathematically describes both the spectral characteristics and the brain sites involved in neuronally rigid dysfunction. This evaluation is conducted by introducing stimulation into the senses, which stimulation changes in known ways, results in surface electrical potentials that can be analyzed as flexibility, and maps the flexibility of the brain's ability to follow the changing stimulation. Mathematical transforms and statistical procedures permit the assessment of neuronal flexibility and inflexibility of the brain at various sites, and empirically tie these qualities to treatment plans. This assessment means introduces stimulation with a known and constantly changing frequency component. In one preferred form, the frequency of the stimulation is set by multiplexed coordination at each of twenty standard brain sites. The responses to the changing stimulation at each brain site are transformed and plotted graphically, allowing brain flexibility to be to be mapped topographically, and the frequency components to be graphed over time.

The treatment disruption involved in this method of neural feedback is brought about by either providing the brain a distorted feedback representation of its true activity, or a means of extending its flexibility and range of functioning. This method connects measurements of brain activity and, when appropriate, real-time measurements of autonomic and other physiological activity, to stimulation of the senses in a way that the measurements of brain activity define and guide the stimulation. This method as well distorts the representation of brain activity returned to it so that the stimulation returned to the brain is a transformation and function of the brain activity, which both disturbs and extends the brain activity beyond its typical pre-treatment or training excursions and functioning. This method as well examines the patterns found in the brain activity and both follows rules and formulates rules to modify the feedback so that the goals of increased flexibility and increased excursion of brain activity are enhanced, while keeping brain functioning within previously-recognized parameters of safe brain functioning. This method, as well, involves nonconscious, involuntary, subcortical process as well as cortical activity, and is very much a passive process. This method, in short, targets brain process and function.

These and other objects, advantages and features of this invention will be apparent from the following description taken with reference to the accompanying drawing, wherein is shown a preferred embodiment of the invention.

BRIEF DESCRIPTION OF THE DRAWING

FIG. 3 is a flow diagram representation of a method thereof for treatment of the individual;

DESCRIPTION OF THE PREFERRED EMBODIMENT

Figure 1:
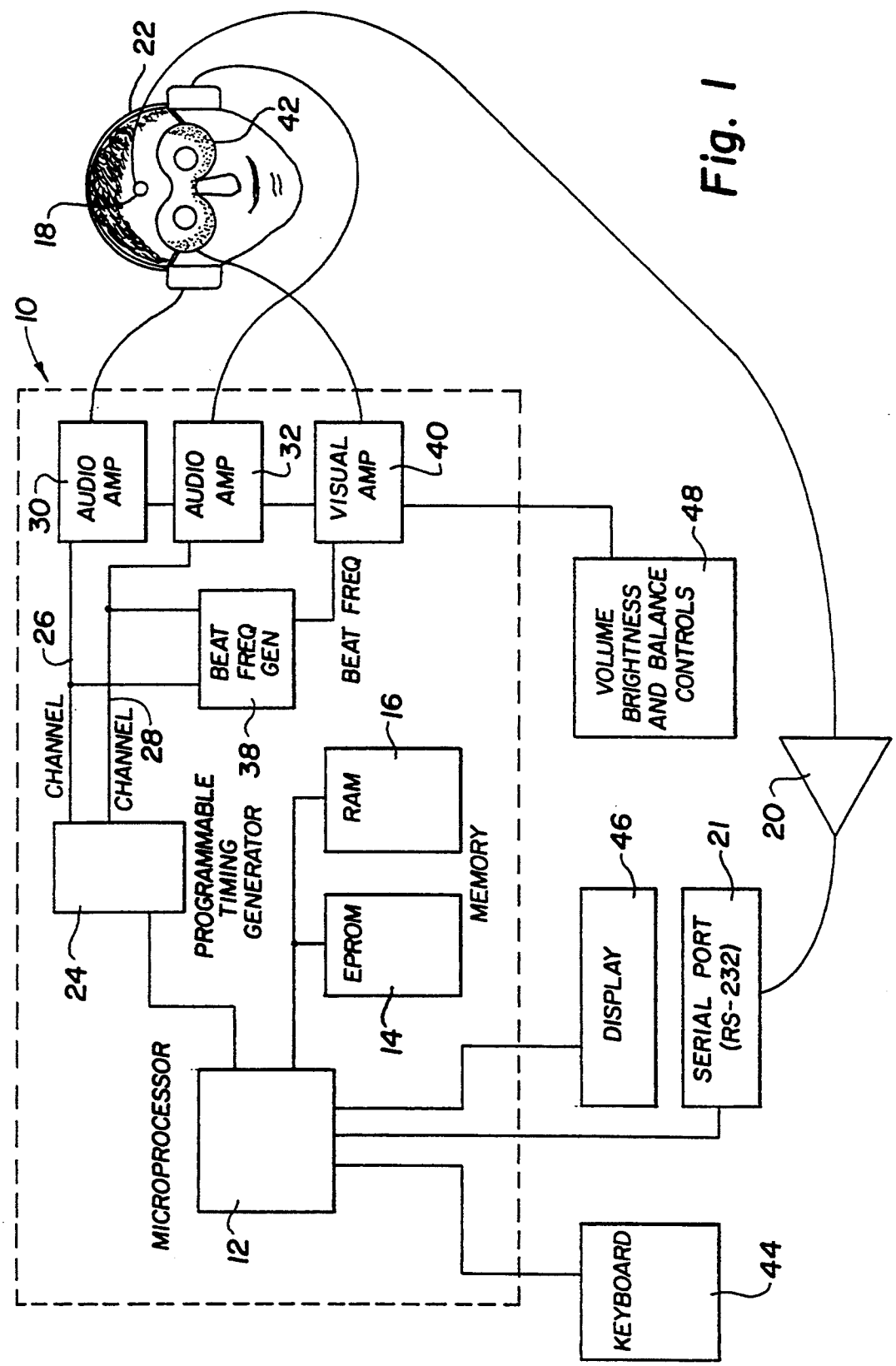
FIG. 1 is a block diagram representation of an apparatus suitable for the method of the current invention.

Referring now to the drawing, and in particular to FIG. 1, an apparatus for practicing a method according to the present invention is represented generally by reference numeral 10 and would be similar to that shown in the Carter/Russell patent. Apparatus 10, which can include a general purpose computer such as any number of personal computers or a special purpose apparatus, includes a computer processor such as microprocessor 12, memory 14 and 16 which can be written to or read from the microprocessor for storing programs and data, and means such as electrode 18 and amplifier 20 for determining a current brain wave of a user 22. Electrode 18 and amplifier 20 communicate with microprocessor 12 through serial port 21. A programmable timing generator 24 is responsive to microprocessor 12 and generates a first signal at a first frequency on a first channel 26 and a second signal at a second frequency on a second channel 28. The frequency difference between the first and second signals is between the current brain wave frequency and the desired brain wave frequency and is within a predetermined range of the current brain wave frequency. First audio amplifier 30 along with right earphone 32 sounds the first signal to the right ear of the user, and second audio amplifier 34 along with left earphone 36 sounds the second signal to the left ear of the user.

The first and second signals are combined in beat frequency generator 38. The combined signal is then amplified by visual amplifier 40, yielding a beat signal equal to the frequency difference which is used to drive light goggles 42. The light or strobe frequency could, of course, be generated directly.

Keyboard 44 and display 46, which can be a conventional computer monitor or a special purpose liquid crystal or other type display, together with Microprocessor 12 and memory 14 and 16 could form part of a personal or even a lap-top computer. Volume, brightness and balance controls 48 are used to adjust to the individual user and the purpose of the use. They could be controlled through the computer rather than directly as shown.

Figure 2:
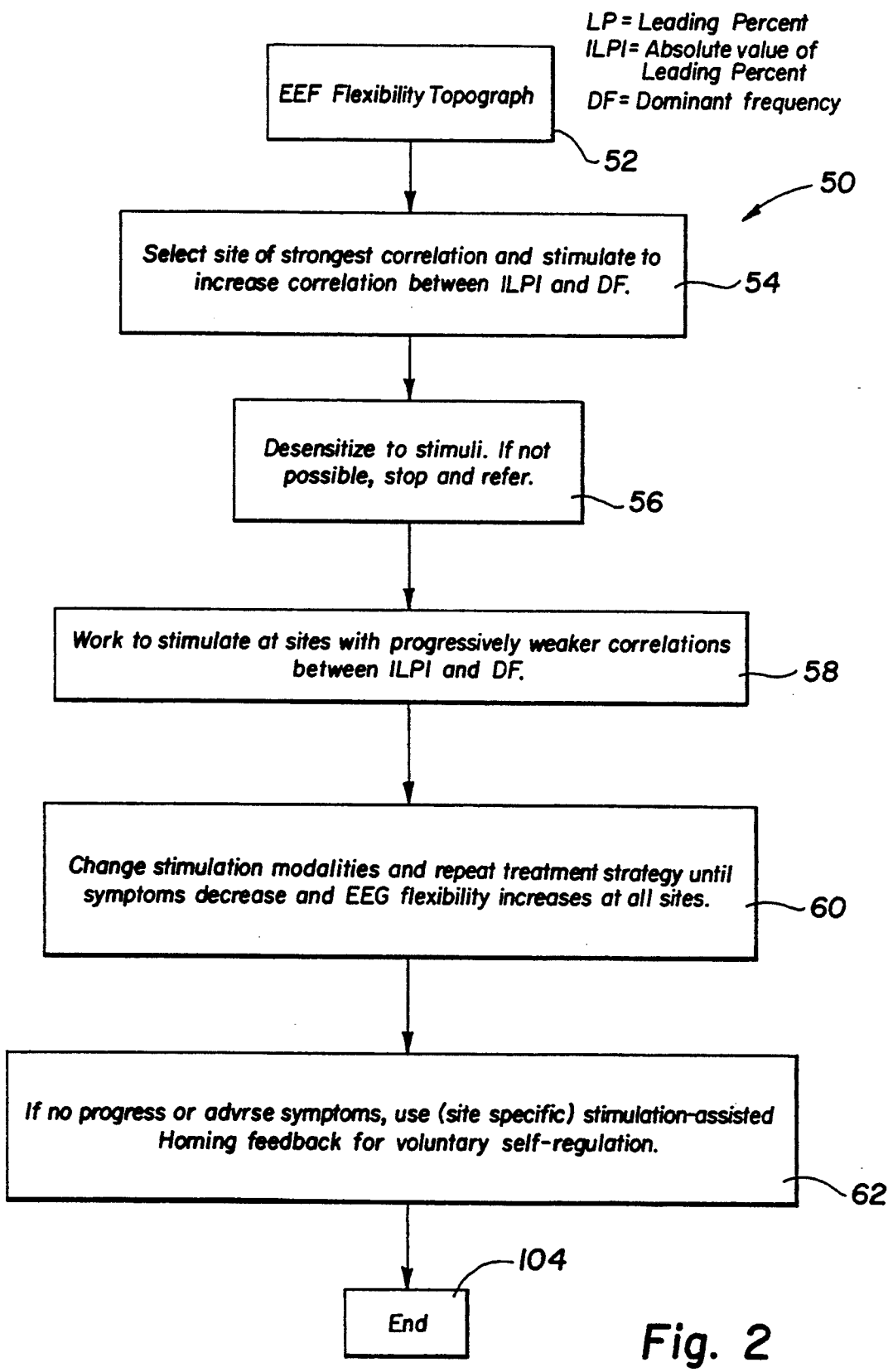
FIG. 2 is a flow diagram representation of an overall method according to the present invention for assessing and treating an individual and, if necessary, desensitizing the individual to certain stimuli.

Referring now to FIG. 2, an overall method according to the present invention for assessing and treating an individual and, if necessary, desensitizing the individual to certain stimuli is referred to generally by reference numeral 50. The overall method includes a method 52 for assessing the individual for flexibility with respect to treatment by electroencephalographic disentrainment feedback, a method 54 for treating the individual and a method 56 for desensitizing the individual to certain stimuli if the individual is otherwise too sensitive for treatment by electroencephalographic disentrainment feedback. Next, steps 58 are taken to stimulate the individual at sites with progressively weaker correlations between the absolute value of the leading percent of the entrainment frequency to the dominant frequency. This can be a matter of simply selecting a new site and repeating process 54 except with the new site. One embodiment of the present invention includes at this point a step 60 of changing the stimulation modality and repeating the overall method for treatment up to this step. One example might be to initially just treating the individual with sound if the individual is sufficiently hypersensitive to light treatment. After the individual has been treated with sound only and has improved EEG flexibility by that means, he or she might then be treated with low level light. Another situation might be for an individual who is especially insensitive to stimulation, one which would initially require full lights and sound, might then be repeated with lights at a lower intensity or without sound.

Finally, if no progress is made or an individual experiences symptoms to the treatment which are adverse, method 50 includes a method 62 for stimulation-assisted homing feedback for voluntary self-regulation.

Referring now to FIG. 3, one method 50 for treating an individual according to the present invention includes first the step 64 of selecting a reference site, which for the embodiment illustrated is the center of the forehead, for determining a brain wave frequency of the individual and placing EEG electrode 18 to the head of the user at that site or where the brain wave of that site may be read. Frequently, simply placing the electrode near the center of the individual's forehead gives satisfactory results which are near the dominant brain wave frequency.

The next step 66 is to set an initial polarity and magnitude for the leading percent at that site. A first sequence 72 of steps is then begun, including the step 68 of measuring the EEG and the step of calculating a Fast Fourier Transform to determine the peak frequency of the individual. A stimulation detectible by the individual with a frequency component at a predetermined difference from the brain wave frequency is then produced. Such a stimulation could be of the conventional sort through light goggles 42 or earphones 22. A strobe light can be produced through the goggles or externally as long as it is sufficiently bright to the individual. The difference of the entraining frequency minus the actual brain wave frequency could be either plus or minus, one polarity is simply picked to be the first polarity, determining if the entrainment is to first lead the brain wave frequency to a higher or a lower frequency.

If a first predetermined time has not elapsed from the initiation of the first sequence of steps and the brain wave frequency has not reached a first limit corresponding to the first polarity, then the first sequence of steps is repeated 76. If, on the other hand, the first predetermined time has elapsed or the brain wave frequency has reached the first limit, then exit the first sequence of steps 78. The polarity of the leading percentage is then changed and its magnitude determined 80. The strobe and beat frequency is then set for the new initial value as step 82. A second sequence of steps is then begun 84 if the individual is not exhibiting signs of being photosensitive. The second sequence of steps is the same as the first sequence but may have different values set for time limit. Either the first or the second sequence of steps can be stopped upon a predetermined stop condition such as end of the session or an adverse reaction by the individual. If the first polarity was positive, entraining the individual's brain wave frequency higher, a reasonable upper limit would be around thirty hertz or even as high as forty hertz. Once that upper limit is reached or the process is timed out in the first direction, the polarity would be changed to negative and the individual's brain wave would then be entrained downwardly to a second limit, perhaps as low as two hertz.

Some individuals exhibit extreme sensitivity to flickering or strobe type lights. In some, such lights can even induce seizures. The person administering treatment needs to remain alert to any symptoms of hypersensitivity. The following types of photosensitive reactions have been observed:

1. feelings of irritability
2. feelings of confusion
3. feelings of anger
4. feelings of fear
5. feelings of lightheadedness
6. headaches
7. anxiety
8. muscle control problems for head injury victims
9. speech interruption problems for head injury victims
10. sleep interruption
11. episodes of increased hypertension. Other, more objective, standards can be used such as step of monitoring skin temperature, skin conductance, heart rate, breathing rate, electromyograph, etc. for significant changes. Certainly, anything more than a 20% change calls for immediate steps.

Figure 5A:
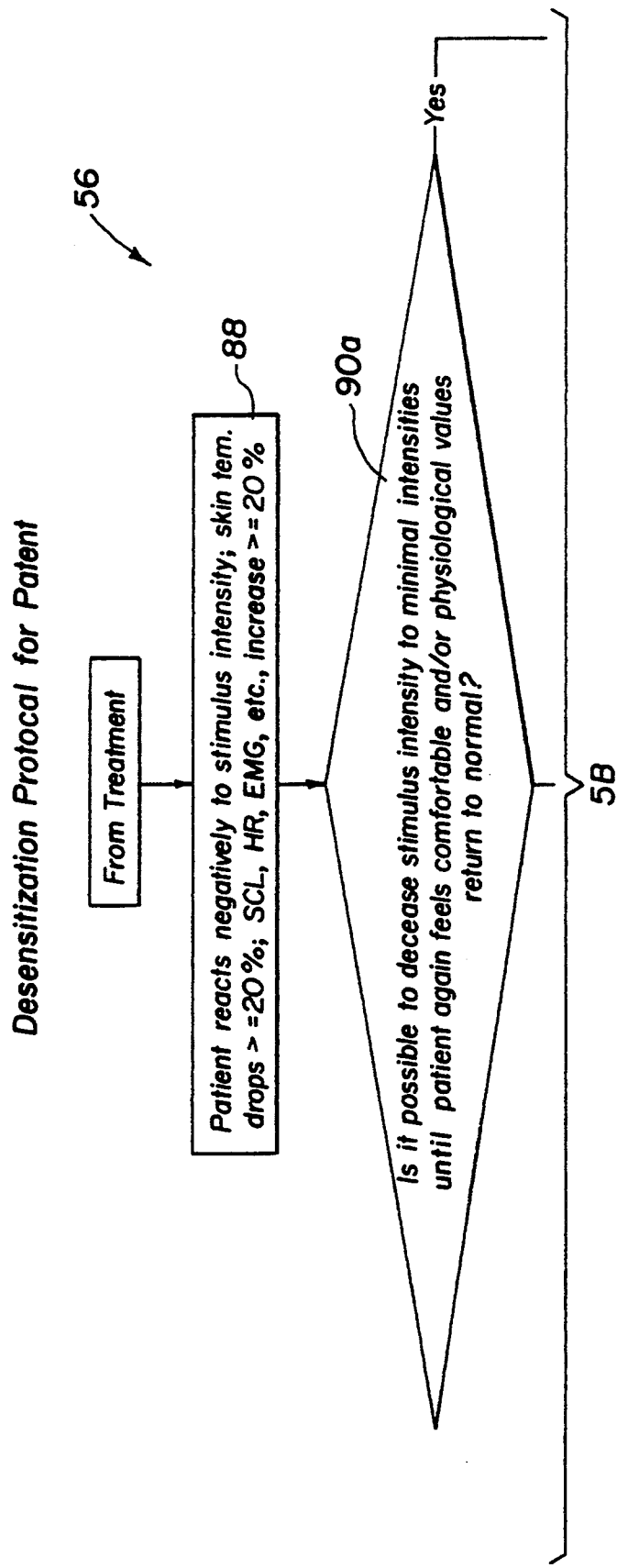
FIG. 5 is a flow diagram representation of a method thereof for desensitizing the individual to certain stimuli.
Figure 5B:
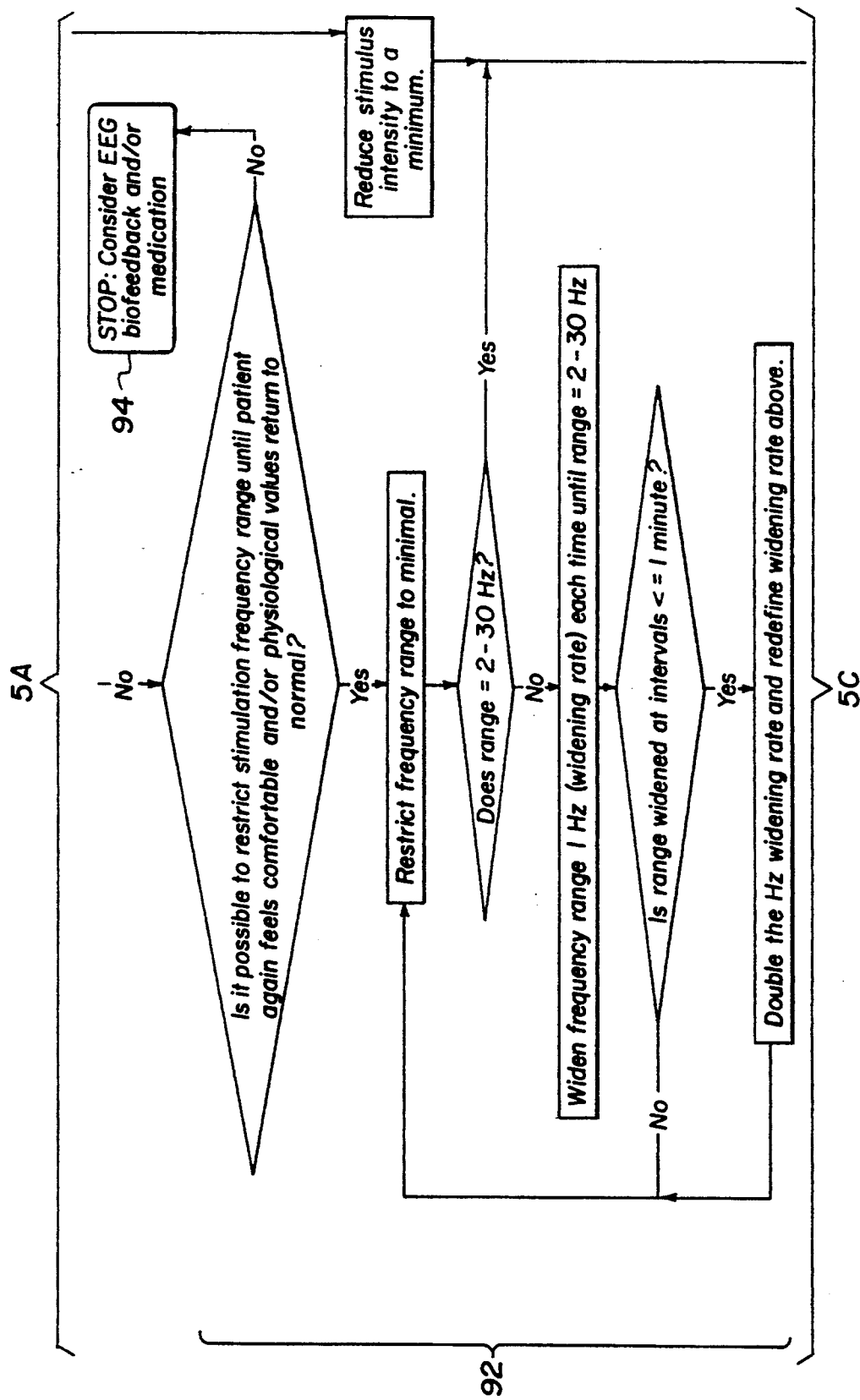
Figure 5C:
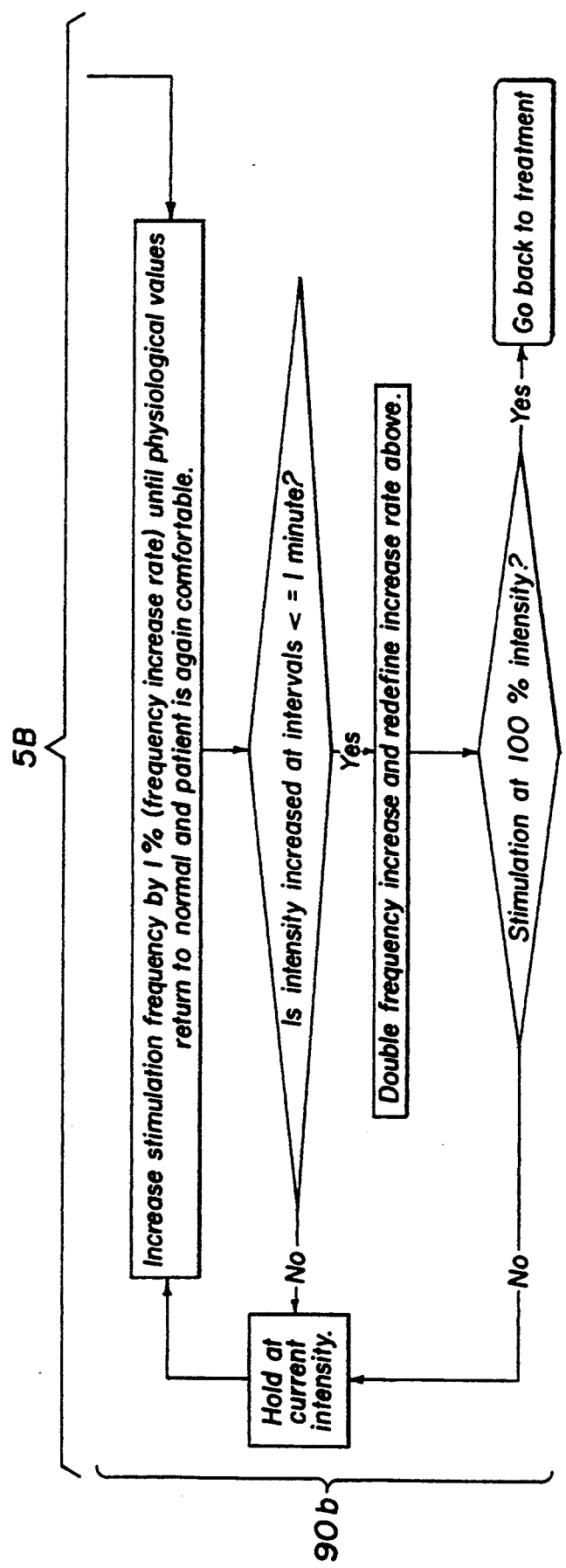

Referring to FIG. 5, certain procedures for dealing with hypersensitivity are built into a preferred process when a strobe is used beginning at 86. If the individual does exhibit signs of being photosensitive, and the lower and mid frequency activity slopes with respect to time are positive, then the intensity of the stimulation is reduced 90 until the slopes are zero or negative. If the individual continues to exhibit signs of being photosensitive, and the lower and mid frequency activity slopes with respect to time continue to be positive, then the frequency excursion limits are reduced 92 until the slopes are zero or negative. If the individual still continues to exhibit signs of being photosensitive, then treatment is stopped 94.

Figure 4B:
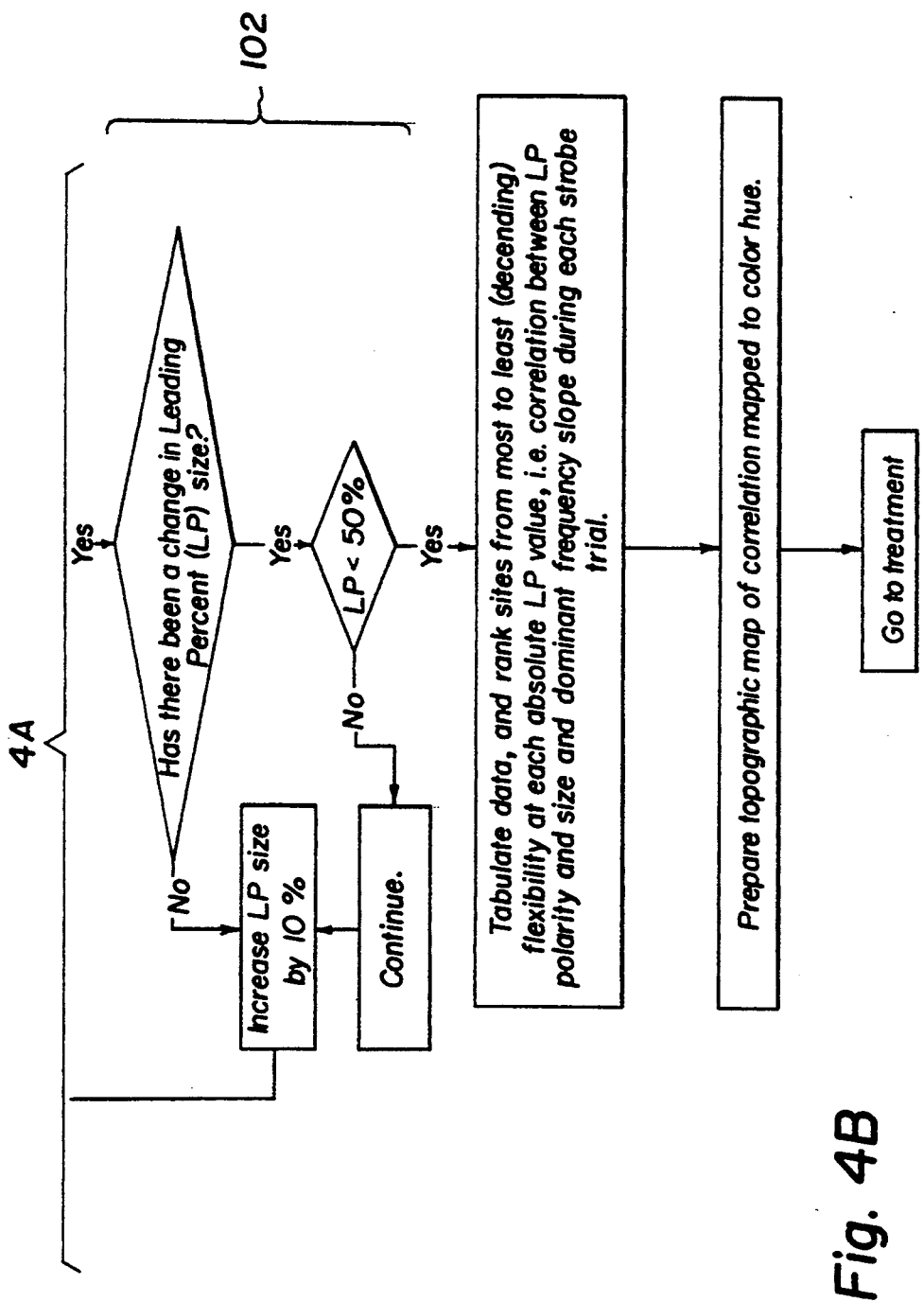
FIG. 4 is a flow diagram representation of a method thereof for assessing the flexibility of the individual with respect to treatment by electroencephalographic disentrainment feedback.

Referring now to FIG. 4, it is normally desirable to assess the flexibility of an individual with respect to treatment by brain wave variation. One such method according to the present invention involves testing several sites on the head of the individual. This can be accomplished with apparatus similar to that already described, but rather than frequently moving single EEG electrode 18, it is more convenient to use a multiple site electrode cap such as ones made by Electrocap International of Eaton, Ohio and covered by U.S. Pat. Nos. 4,085,739 and 4,323,076. The first step 96 after selecting an initial site is to determine a brain wave frequency of the individual. This step is repeated for all sites to be tested 98, both polarities 100 and for leading percent sizes 102 up to a maximum, in this case 50%. Stimulation detectible by the individual is begun with a frequency component at an initial difference from the brain wave frequency, the difference being at a first polarity as before. A sequence of steps is started by recording the brain wave frequency at the selected site. If the predetermined sites have not all been selected for the current frequency and polarity, then use a site which has not been selected and repeat the sequence of steps from the beginning. If the predetermined sites have all been selected for the current frequency and polarity, then determine if there has been a polarity change for the current frequency. If there has not been a change in polarity for the current frequency, then change the polarity and repeat the sequence of steps from the beginning. If, to the contrary, there has been a change in polarity for the current frequency, then determine if there has been a change in the difference in frequency. If there has not been a change in the difference in frequency, then increase the difference in frequency by a first predetermined amount or a first predetermined percentage, in this case 10%. Change the polarity and repeat the sequence of steps from the beginning. If there has been a change in the difference in frequency, then determine if the difference in frequency is less than a second predetermined amount or a second predetermined percentage, in the particular case illustrated, 50%. If the difference in frequency is not less than the second predetermined amount or the second predetermined percentage, then increase the difference in frequency by the first predetermined amount or the first predetermined percentage, change the polarity and repeat the sequence of steps from the beginning. If the difference in frequency is less than the second predetermined amount or the second predetermined percentage, then make a determination of flexibility according to predetermined criteria. Such criteria might depend on how rapidly the brain of the individual disentrains or how far the maximum excursion extends for different sites.

Figure 6:
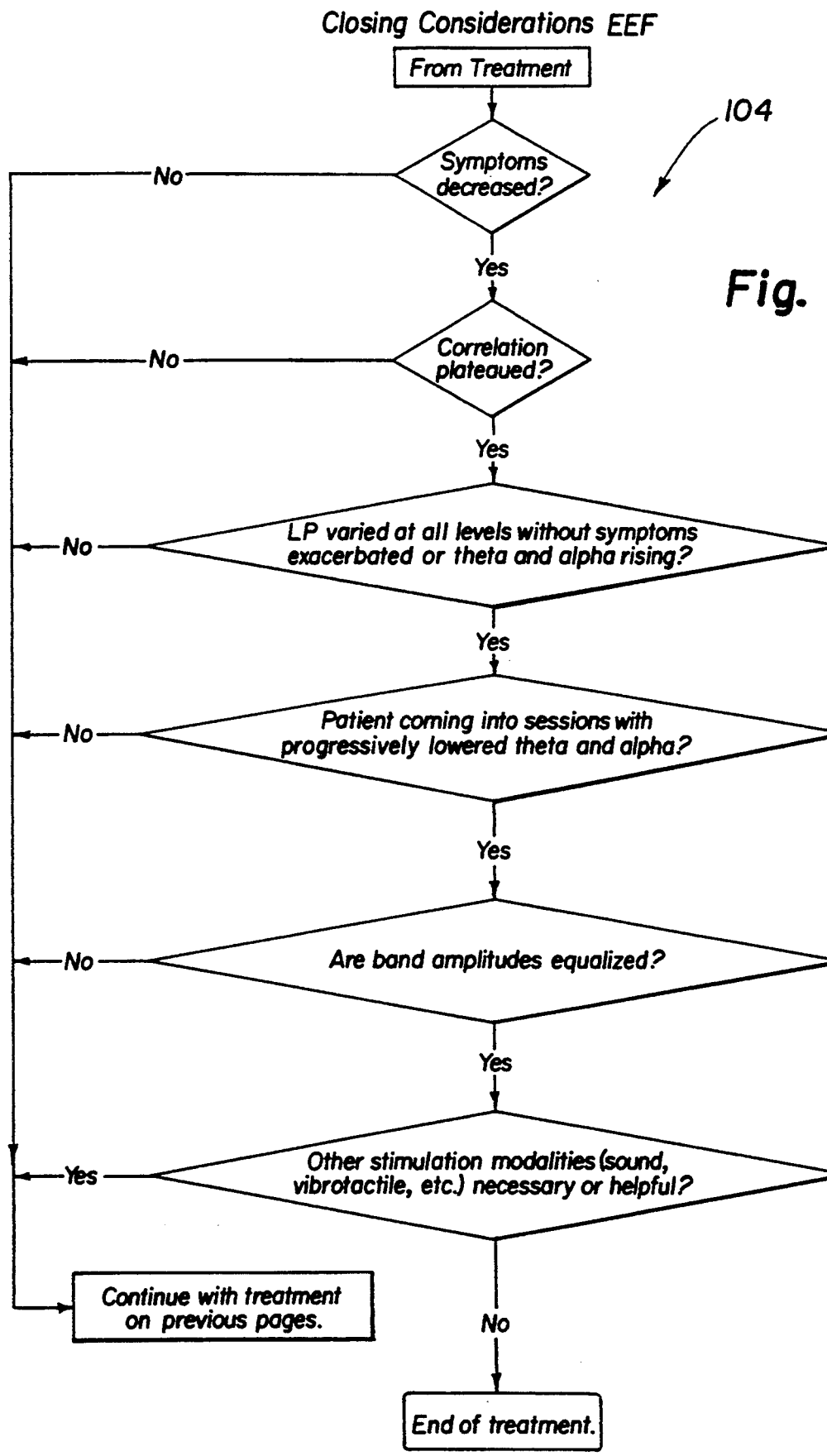
FIG. 6 is a flow diagram representation of a method thereof for determining if further evaluation or treatment of the individual is needed.

Finally, referring to FIG. 6, certain closing considerations are part of the preferred process and referred to by reference numeral 104.

EXAMPLE 1

As one specific example of a method according to the present invention, there are clinical situations in which it is ultimately desirable to have reasonably high amplitudes of low frequency activity. "Ultimately" is emphasized because under some specific conditions the lowering of frequency activity has been shown to be proper only after the percentage of high frequency activity is initially raised. The conditions for the raising of the EEG are here described before those that will benefit by its lowering. These conditions apply when the following disorders are discovered to be accompanied by underlying attention deficit disorder characterized by problems with memory, attention, concentration:

post-traumatic stress
depression
addiction.

For these problems, the amplitude of the high frequency EEG should be raised until there is observed an improvement in memory, attention and concentration. Typically, the feedback frequency is set between 105% and 150% of the EEG frequency. After the work on higher frequency enhancement is finished, lower frequency entrainment, setting the leading frequencies between 95% and 50% of the EEG frequency, will often bring with it thought and behavior which the patient has avoided for many years: physical symptomatology flare-ups, emotional reactions, perceptual distortions, mood changes, etc. Although these will be clearly noticed—usually after the third or fourth ten minute session—these experiences have often been quite tolerable to the patients to the extent that they have not typically defended themselves against them.

On the rare instance when there has been continued or exacerbated defensiveness, the strobe stimulus was terminated after 60 seconds and patients have discovered underlying emotions which were then quite manageable. It was important to stop the feedback under these conditions so that the feedback did not become a distracter and artificial defense.

The method of EEG disentrainment feedback according to present invention has also been used with higher frequency enhancement for the following disorders:

attention deficit
seizure
migraine
post-concussive impairment
anxiety
appetite intrusiveness (to suppress appetite).

Sessions usually last ten minutes initially to acclimate the individual, but they may go as long as twenty or thirty minutes of connect time.

From the foregoing it will be seen that this invention is well adapted to attain all of the ends and objectives hereinabove set forth, together with other advantages which are inherent to the apparatus.

It will be understood that certain features and sub combinations are of utility and may be employed without reference to other features and sub combinations. This is contemplated by and is within the scope of the claims.

As many possible embodiments may be made of the invention without departing from the scope thereof, it is to be understood that all matter herein set forth or shown in the figures of the accompanying drawings is to be interpreted as illustrative and not in a limiting sense.

I claim:

1. A method for treating an individual, comprising in combination the steps of:

selecting at least one reference site for determining a brain wave frequency of the individual;

beginning a first sequence of steps, wherein the first sequence of steps is stopped upon a predetermined stop condition;

producing a stimulation detectible by the individual with a frequency component at a predetermined difference from the brain wave frequency, the difference being at a first polarity;

determining if a first predetermined time has elapsed from the initiation of the first sequence of steps;

determining if the brain wave frequency has reached a first limit corresponding to the first polarity;

if the first predetermined time has not elapsed and the brain wave frequency has not reached the first limit, then repeating the first sequence of steps;

if the first predetermined time has elapsed or the brain wave frequency has reached the first limit, then beginning at least one second sequence of steps, wherein either the first or the second sequence of steps is stopped upon a predetermined stop condition;

producing a stimulation detectible by the individual with a frequency component at a predetermined difference from the brain wave frequency, the difference being at a second polarity which is opposite to the first polarity;

determining if a second predetermined time has elapsed from the initiation of the second sequence of steps;

determining if the brain wave frequency has reached a second limit corresponding to the second polarity;

if the second predetermined time has not elapsed and the brain wave frequency has not reached the second limit, then repeating the second sequence of steps;

if the second predetermined time has elapsed or the second reference brain wave frequency has reached the second limit, then beginning the first sequence of steps.

2. A method according to claim 1 wherein:

one of the polarities is positive and the other polarity is negative; and the limit corresponding to the positive polarity is less than forty hertz and the limit corresponding to the negative polarity is greater than two hertz.

3. A method for treating an individual, comprising in combination the steps of:

selecting a reference site for determining a brain wave frequency of the individual;

beginning a first sequence of steps, wherein the first sequence of steps is stopped upon a predetermined stop condition;

producing a stimulation detectible by the individual with a frequency component at a predetermined frequency difference from the reference site for determining a brain wave frequency at a first polarity;

determining if a first predetermined time has elapsed from the initiation of the first sequence of steps;

if the first predetermined time has not elapsed, then repeating the first sequence of steps;

if the first predetermined time has elapsed, then beginning a second sequence of steps, wherein the second sequence of steps is stopped upon a predetermined stop condition;

producing a stimulation detectible by the individual with a frequency component at a predetermined difference from the brain wave frequency at a second polarity which is opposite to the first polarity;

determining if a second predetermined time has elapsed from the initiation of the second sequence of steps;

if the second predetermined time has not elapsed, then repeating the second sequence of steps;

if the second predetermined time has elapsed, then beginning the first sequence of steps.

4. A method according to claim 3 wherein: the brain wave frequency is the dominant brain wave frequency; and one of the polarities is positive and the other polarity is negative.

5. A method for treating an individual comprising in combination the steps of:

placing an electroencephalogram electrode to the head of the individual;

arranging a strobe light detectable by the individual;

setting a leading percentage polarity and magnitude from the brain wave frequency at that site;

beginning a first sequence of steps by measuring the brain wave frequency of the individual at the site;

determining the peak brain wave frequency;

initializing a strobe frequency using the leading percentage size and polarity as set;

if a predetermined time has not elapsed since the polarity of the leading percentage was last set, then beginning the first sequence of steps;

if the predetermined time has elapsed since the polarity of the leading percentage was last set, then changing the polarity and setting the magnitude;

initializing the strobe frequency using the leading percentage size and polarity as set;

if the individual does not exhibit signs of being photosensitive, then repeating the first sequence of steps; and if the individual does exhibit signs of being photosensitive, and lower and mid frequency activity slopes with respect to time are positive, then reducing the intensity of the stimulation until the slopes are zero or negative;

if the individual continues to exhibit signs of being photosensitive, the lower and mid frequency activity slopes with respect to time continue to be positive, then reducing the frequency excursion limits, until the slopes are zero or negative; and if the individual still continues to exhibit signs of being photosensitive, then stopping treating.

6. A method for assessing the flexibility of an individual with respect to treatment by electroencephalographic disentrainment feedback:

selecting an initial site from a plurality of predetermined sites for determining a brain wave frequency of the individual;

producing a stimulation detectible by the individual with a frequency component at an initial difference from the brain wave frequency, the difference being at an initial polarity;

beginning a sequence of steps by recording the brain wave frequency at the selected site;

if the plurality of predetermined sites have not all been selected for the stimulation frequency and polarity, then selecting a site which has not been selected and repeating the sequence of steps from the beginning;

if the plurality of predetermined sites have all been selected for the stimulation frequency and polarity, then determining if there has been a polarity change for the stimulation frequency;

if there has not been a change in polarity for the stimulation frequency, then changing the polarity and repeating the sequence of steps from the beginning;

if there has been a change in polarity for the stimulation frequency, then determining if there has been a change in the difference in frequency;

if there has not been a change in the difference in frequency, then increasing the difference in frequency by a first predetermined amount or a first predetermined percentage, changing the polarity and repeating the sequence of steps from the beginning;

if there has been a change in the difference in frequency, then determining if the difference in frequency is less than a second predetermined amount or a second predetermined percentage;

if the difference in frequency is not less than the second predetermined amount or the second predetermined percentage, then increasing the difference in frequency by the first predetermined amount or the first predetermined percentage, changing the polarity and repeating the sequence of steps from the beginning;

if the difference in frequency is less than the second predetermined amount or the second predetermined percentage, then making a determination of flexibility according to predetermined criteria.

* * * * *